US008715734B2

(12) United States Patent
Schwarz

(10) Patent No.: US 8,715,734 B2
(45) Date of Patent: *May 6, 2014

(54) AMOXICILLINE INSTANT GRANULATE

(75) Inventor: Franz Xaver Schwarz, Wörgl (AT)

(73) Assignee: Sandoz AG, Basel (CH)

( * ) Notice: Subject to any disclaimer, the term of this patent is extended or adjusted under 35 U.S.C. 154(b) by 1307 days.

This patent is subject to a terminal disclaimer.

(21) Appl. No.: 10/589,924

(22) PCT Filed: Feb. 23, 2005

(86) PCT No.: PCT/EP2005/001894
§ 371 (c)(1),
(2), (4) Date: Aug. 18, 2006

(87) PCT Pub. No.: WO2005/079768
PCT Pub. Date: Sep. 1, 2005

(65) Prior Publication Data
US 2007/0160673 A1    Jul. 12, 2007

(30) Foreign Application Priority Data
Feb. 24, 2004  (SI) .................................. 200400061

(51) Int. Cl.
*A61K 9/14* (2006.01)
(52) U.S. Cl.
USPC ........................... 424/489; 424/408; 424/409
(58) Field of Classification Search
None
See application file for complete search history.

(56) References Cited

U.S. PATENT DOCUMENTS

| 4,177,254 A | 12/1979 | Khan et al. |
| 6,242,382 B1 * | 6/2001 | Bratz et al. ..................... 504/133 |
| 7,157,094 B2 * | 1/2007 | Gaytan ........................ 424/408 |
| 2002/0006433 A1 | 1/2002 | Davidson et al. |

FOREIGN PATENT DOCUMENTS

| EP | 0 080 862 | 6/1983 |
| WO | WO 03/063820 | 8/2003 |
| WO | WO 2004/047808 | 6/2004 |

OTHER PUBLICATIONS merriam-webster.com/dictionary/wet; definition of "wet", Nov. 1, 2011.*
Tyle, "Effect of size, shape and hardness of particles in suspension on oral texture and palatability," Acta Psychologica 84 (1993) pp. 111-118.

* cited by examiner

*Primary Examiner* — Hasan Ahmed
(74) *Attorney, Agent, or Firm* — Jeffrey S. Melcher; Manelli Selter PLLC

(57) ABSTRACT

A novel process for preparing stable granulate which comprises amoxicillin trihydrate and a sugar, and to novel stable granulate comprising amoxicillin trihydrate and the sugar as well, for reconstitution with water into fine stable homogeneous aqueous suspension is described. The novel process omits preliminary process step for preparing fine particle size of micronized amoxicillin trihydrate used subsequently in the granulation process known in the art, for example grinding or micronizing of said antibiotic. In a preferred aspect of the invention the novel stable granulate comprises amoxicillin trihydrate and the sugar, preferably sucrose, free of any pharmaceutically acceptable excipient. Novel granulate, which is easily dissolved in water to form smooth aqueous suspension immediately, is used for treating bacterial infections in humans or animals, especially in pediatric patients and in the geriatrics.

20 Claims, 1 Drawing Sheet

AMOXICILLINE INSTANT GRANULATE

FIELD OF THE INVENTION

Figure 1:
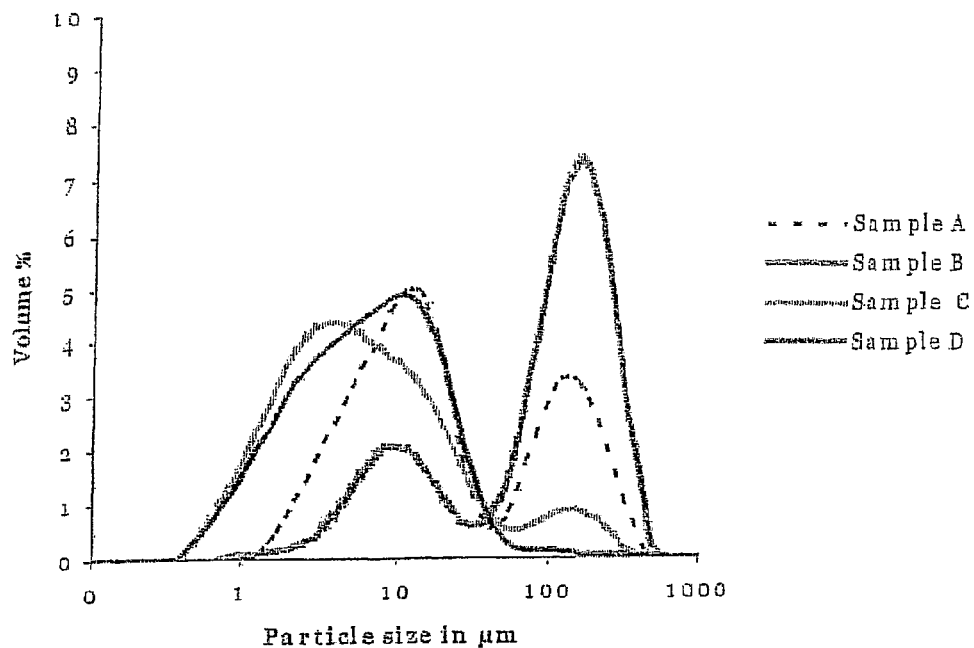

The present invention relates to a novel process for preparing pharmaceutical granulate comprising amoxicillin trihydrate and a sugar, to a novel stable granulate comprising amoxicillin, preferably amoxicillin trihydrate and the sugar, for reconstitution with water into oral aqueous suspension formulation and to a method of treatment of bacterial infection in humans or animals.

TECHNICAL PROBLEM

There is a constant need for preparing stable oral fine aqueous suspension comprising amoxicillin trihydrate, with palatable taste for use in pediatric patients and in the adults, especially in the geriatrics, obtained after reconstitution of granulate comprising amoxicillin trihydrate into aqueous suspension. Aqueous suspensions of said β-lactam antibiotic known in the art can be obtained by the reconstitution of granular product with water, wherein said antibiotic used for the preparation of granulate have to be preliminary prepared by way of grinding or micronising of said antibiotic and/or the addition of surface active substances to the composition in order to obtain applicable aqueous suspension formulations after reconstitution of granulate with water.

PRIOR ART

Amoxicillin is an antibacterial agent extensively used for the treatment of a wide range of bacterial infections. Amoxicillin in the form of the trihydrate is available on the market in a number of different formulations, for example, as granules or powders for oral suspension, hard gelatin capsules, tablets, chewable tablets, pediatric drops. Different formulations and different amounts of amoxicillin are provided for adult and pediatric patients. Depending on the indications, the weight of the amoxicillin (as amoxicillin trihydrate) in unit dosage form for children and adults may range from 125 mg to 3 g. The largest film-coated tablet that can be manufactured contains a maximum of 1 g of the active substance. Children are unable, or to find it very difficult, to swallow tablets of that size. The problem with swallowing increases with the age of the patient and is found in the geriatric patients. For pediatric patients each 5 ml of reconstituted aqueous suspension comprising either 125 mg or 250 mg of amoxicillin as the trihydrate.

Aqueous suspensions of amoxicillin trihydrate, obtained after reconstitution of water-soluble granulate in water, are mainly used in treating children and in elderly patients. Prior to administration to patients granulates comprising said β-lactam antibiotic for oral administration are suspended in an aqueous liquid. In this cases amoxicillin (as trihydrate) is usually mixed with suspension stabilisers (e.g. hydrocolloids or thickeners), buffers, preservatives, aromatic substances etc., together with a considerable amount of sugar, for example sucrose, and/or lactose, sugar alcohols, for example manitol or sorbitol, and maltodextrins to form granules being reconstitutable into aqueous suspension. The speed of absorption after administration of aqueous suspension of antibiotic to a patient is to a large extent dependent on the particle size of the crystals of said β-lactam antibiotic, on their wettability and on their suspensibility. A very fine aqueous suspension is required to achieve rapid absorption after administration to a patient.

Generally, this known object is obtained by way of preliminary step of grinding or micronizing of an antibiotic and/or the addition of surface active substances to the composition. More preferably, a micronized amoxicillin trihydrate is used in common granulating methods for preparing granulate, typically the majority of particles size of antibiotic in the granulate being less than 50 μm. Jato J. L. Vila and Pacheco R. Martinez, Ciencia & Industria Farmaceutica (1976), 8(11), 330-332, describes effect of particle size on the dissolution rate of amoxicillin trihydrate.

Normally, aqueous suspension formulations described in the prior art, lacks of suspension stability (the tendency to separate the active compound out again) and poor flowability of granular product, and for that object to obtain homogeneous and stable granules common granulating method such as wet granulation technique are used in the prior art processes. In order to obtain said object wet granulation process technique have to be carried out very carefully to avoid the agglomeration of the crystals of the antibiotic and, consequently, the formation of large, secondary particles of active substance with slow solubility and/or suspendability.

It is known from the prior art that granulate comprising active substance, e.g. amoxicillin trihydrate, which is filled into a suitable, single dose units, such as glass bottles, sachets, plastic tubes, for administration, or alternatively the granular formulations may be filled in jars as a multidose presentation for reconstitution into aqueous suspension. Shortly before the administration to the patients water is added to the granular formulation and the resulting dissoluted product is shaken well to prepare an oral aqueous suspension. Various pharmaceutically acceptable excipients are necessary as the additive added during common granulation processes, for example lubricants, flavouring agents, sweetening agents, thickeners, suspending agents, disintegrants, desiccants, colours, dyes, preservatives, binders, to obtain granulate and further to achieve a good distribution of antibiotic into granulate to ensure stability of the resulting aqueous suspension during the period of administration to the patients and to prevent the growth of microorganisms during the time.

Aqueous suspensions of amoxicillin trihydrate prepared according to the processes known in the art contain antibiotic highly concentrated that not all of it dissolves in water. Dosage is normally carried out using a measuring spoon or, for smaller volumes, by means of a dosing syringe.

Granules containing penicillin, e.g. amoxicillin trihydrate being reconstitutable into aqueous suspension formulation and a process for their preparation by fluid bed granulation is described in U.S. Pat. No. 4,177,254. According to said process obtained granules contain particles or agglomerates of particles. Aqueous suspension obtained after reconstitution of granules in water suffers of lower speed of absorption and of other known drawbacks, described in the prior art.

The preparation of granules comprising amoxicillin trihydrate has been described in WO 92/19227 and WO 98/35672 wherein in a preferred process granules are prepared by roller compaction. WO 00/66169 describes a chewable tablet comprising amoxicillin in which the chewable base comprise essentially mannitol which is present in at least 25% by weight of the tablet useful for treating a wide range of bacterial infections in children. WO 03/063820 describes a process for the production of a granulate which is stable to segregation and which comprises granulate particles, which contain at least one β-lactam antibiotic, e.g. amoxicillin in the form of a trihydrate and at least one β-lactamase inhibitor, useful for the production of pharmaceutical compositions.

DESCRIPTION OF THE INVENTION

The object of the present invention is to find a novel process for preparing stable granulate comprising amoxicillin trihydrate and to stable granulate comprising amoxicillin trihydrate as well, for reconstitution with water, to obtain fine stable homogeneous aqueous suspension, wherein the preliminary process step for preparing fine particle size of micronized antibiotic amoxicillin trihydrate used subsequently in the granulation processes as described in the art, for example grinding or micronizing, would be omitted.

Further is the object of the present invention to prepare stable granulate with good flow characteristics comprising amoxicillin trihydrate, wherein the addition of common pharmaceutically acceptable excipients known in the art, for example thickeners, lubricants, disintegrants, preservatives, desiccants, stabilizing agents, flavouring agents, dyes, suspending agents etc. would be also omitted and resulting granules would enable very rapid formation (e.g. from 10 to 60 seconds) of an aqueous suspension in a small volume of water and the resulting aqueous suspension comprising amoxicillin trihydrate would be highly palatable and consequently easily swallowed by the patient, preferably by children and elder patients.

We have surprisingly and unexpectedly found that the problem known in the prior art can be solved by the novel process of the present invention, wherein amoxicillin trihydrate is compacted with a water soluble sugar or combinations of sugars, that is monosaccharides, disaccharides, oligosaccharides or polysaccharides, by means of commercially available extruder. Preferably, according to the novel process of the present invention amoxicillin trihydrate is compacted with the sugar (carbohydrate), preferably selected from the group consisting of sucrose, lactose, manitol, sorbitol, fructose, glucose, trehalose and maltodextrin alone or in combination, by means of said commercially available extruder, wherein the loss of crystallisation water of amoxicillin trihydrate caused by applied pressure and temperature between 30° to 100° C. is compensated for by the addition of water. The resulting granulate is reconstituted prior to use with water into stable, homogeneous, fine and pleasant tasting aqueous suspension of amoxicillin trihydrate for human and animal patients, preferably in pediatric patients and in geriatrics.

More preferably, the granulate of the invention comprise sucrose as the sugar component.

Among the sugar alcohols manitol and sorbitol are preferably used for preparing granulate.

According to the process of the present invention an extrusion granulation is performed and water or aqueous solution of sugars, preferably sucrose, may be used as a granulation liquid to obtain an extruded wet granulation mass. A granulation mass appropriate for extrusion granulation may be obtained by mixing and sieving amoxicillin trihydrate and sugar, preferably sucrose, extruding obtained sieved mixture with water or aqueous solution of the sugar as extrusion granulation liquid. Preferably sucrose may be used as the sugar, but other sugar(s) alone or in combinations of sugars, as described above, may be used as well. The amount of granulating liquid may be easily determined. The granulation mixture is extruded, e.g. at appropriate extrusion temperatures, e.g. between 30° to 100° C., to obtain wet extruded mass of amoxicillin trihydrate. The obtained wet extruded mass is screened through a sieve, preferably oscillating sieve, subsequently dried the obtained sieved extruded wet mass which is screened again through a sieve, preferably oscillating sieve. Dried and sieved extruded mass is homogenized to obtain granulate comprising amoxicillin trihydrate. A preferred mesh size of the sieve used in the process is in the range between 0.5 mm to 4.0 mm, preferably in the range of 1 mm to 2 mm.

Amoxicillin trihydrate in the form of granulate for reconstitution with water into aqueous suspension may be prepared according to a process of the present invention comprising the steps:
a. sieving the mixture of amoxicillin trihydrate and the sugar
b. extruding said sieved mixture with water or aqueous solution of sugar as a granulation liquid to obtain a wet extruded mass,
c. screening the wet extruded mass through a sieve
d. drying the sieved wet extruded mass
e. dried and sieved extruded mass is homogenized to the granulate
f. obtained granulate are easily dissolved in water to form smooth suspension immediately.

We have unexpectedly found that according to the process of the invention the fine micronized particles of amoxicillin trihydrate are obtained in the course of novel process itself and the preliminary process step known in the art, for example grinding or micronizing of said antibiotic necessary for subsequent granulation process, is omitted.

We have also unexpectedly found that other pharmaceutically acceptable excipients such as commonly used in pharmaceutical formulation technology for granulation process as described above, may be omitted as well. Preferably, no pharmaceutically acceptable excipient is added during the whole extrusion granulation process in order to obtain granulated amoxicillin trihydrate and the sugar, free of any excipient. Granulate obtained in the process of the present invention is stable even without addition of any stabilizing agent or other excipients. With good reason we may designate the novel granulate of the present invention "amoxicillin instant granulate".

The micronized particles of amoxicillin in the granulate obtained according to the process of the present invention are in the size range between 0.1 μm to 100 μm, preferably between 0.5 μm to 50 μm.

Preferred amoxicillin granulate comprise from 1 to 80 weight %, preferably between 5 to 50 wt. %, more preferably between 10 to 30 wt. % of amoxicillin trihydrate and from 20 to 99 weight %, preferably from 70 to 90 wt. % of sucrose.

In one aspect, amoxicillin granulate comprise from 20 to 90%, preferably between 70 to 90% of the water soluble sugar, selected from the group consisting of sucrose, lactose, manitol, sorbitol, fructose, glucose and maltodextrin alone or in combination. Mixtures of said sugars and sucrose may also be used.

A preferred mean particle size of the granules is in the range between 200 μm to 3000 μm, particularly between 500 μm to 1500 μm.

Aqueous suspensions comprising amoxicillin trihydrate and the sugar obtained after reconstitution of granulate of the present invention with water are suitable even for the administration of larger amounts of the antibiotic, for example 5 g in 50 ml suspension.

In a further aspect, the present invention provides a process for the production of novel granulate, comprising optionally adding further pharmaceutically acceptable excipient(s) to a granulate afterwards e.g. for admixing said excipients with the granulate obtained by a process according to the present invention if for the final application of aqueous suspension formulation of said β-lactam antibiotic such a formulation would be suitable for human or animal patients.

The process of the present invention provide a solid suspension of fine micronized particles of amoxicillin trihydrate in sugars, preferably in the sugar, selected from the group consisting of sucrose, lactose, manitol, sorbitol, fructose, glucose and maltodextrin alone or in combinations, more preferably in sucrose. The micronized particle size of said β-lactam antibiotic after dissolution of resulting granulate with water into aqueous suspension corresponds to that of dry amoxicillin trihydrate obtained by preliminary process step of micronizing the antibiotic.

In a further aspect, antibiotic may be pre-wetted with the sugar to obtain a granulate and when said granulate is dissolved in water, ensures rapid formation of a homogeneous aqueous suspension of amoxicillin trihydrate.

The fineness, homogeneity and good perfusion provide an aqueous suspension of amoxicillin obtained after reconstitution of granulate with water, and obtained suspension is considerably less prone to sedimentation of the particles of antibiotic, even without addition of thickeners and other pharmaceutically acceptable excipients.

Rapidly obtained, fine aqueous suspension of the present invention ensures good and stable bioavailability of amoxicillin trihydrate, irrespective of the storage time of the obtained aqueous suspension.

Figure 2:
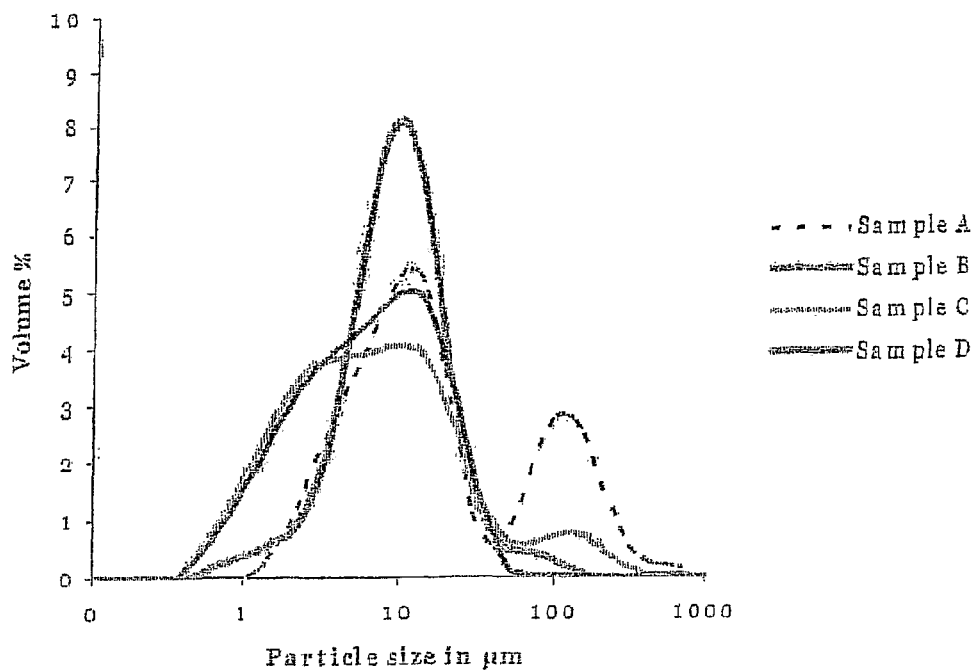

FIG. 1 and FIG. 2 show the comparison between the distribution of micronized particle size of amoxicillin trihydrate in aqueous suspension obtained immediately after reconstitution of granulate with water and after storage of obtained aqueous suspension for 24 hours. From the comparison of both Figures it is easily seen that only granules obtained according to the novel process of the present invention (sample D) lead to an aqueous suspension without formation of any major agglomerates. All particles of said β-lactam antibiotic in the suspension are in the size of less than 50 μm, the major particles being within the range from 1 μm to 30 μm, even shortly after reconstitution of granules with water into aqueous suspension and which shows no alteration during storage.

In FIGS. 1 and 2 sample A means the distribution of particles size of amoxicillin trihydrate obtained after reconstitution of granulate into aqueous suspension, wherein said granulate is obtained according to wet granulation technique, known in the art. Sample B means the distribution of particle size of antibiotic obtained after reconstitution with water of dry mixture of mainly saccharose, xanthan gum and surfactant (glycerolmonooleate) with micronized amoxicillin trihydrate which micronized antibiotic is obtained preliminary by the methods known in the art. Sample C means the distribution of particle size of antibiotic obtained after reconstitution of the mixture of preliminary untreated amoxicillin trihydrate and sucrose into aqueous suspension and sample D means the distribution of particle size of amoxicillin trihydrate obtained after reconstitution of the novel granulate of the present invention into aqueous suspension.

The granulate obtained according to the present invention is filled into glass bottles, packed in unit dose sachets or other suitable container. A granular product may be used at a range of unit doses, for example 125 mg, 250 mg, 500 mg, 1 g and 3 g of amoxicillin trihydrate. The dosage forms makes it very easy to prepare also large amounts of antibiotic in relatively small quantities of water for patient friendly administration.

In a further aspect, homogeneous diluted aqueous suspensions or solutions of amoxicillin trihydrate may be obtained rapidly by simple stirring of granulates of the present invention with drinking water for the treatment of bacterial infections in animals and domestic animals such as cattle, calves, horses, pigs, sheep, lambs, dogs, cats, poultry /chickens, ducks, geese, turkeys.

Obtained diluted aqueous suspensions or solutions of amoxicillin trihydrate according to the present invention are stable for several days, up to 14 days at room temperature.

The invention also provides granulate comprising amoxicillin trihydrate and the sugar and aqueous suspensions obtained by reconstitution of said granulate with water for use in the treatment of bacterial infections.

The invention also provides a method of treatment of bacterial infections in humans and animals which comprises the administration of aqueous suspensions obtained by reconstitution of granulates, comprising therapeutically effective amount of amoxicillin trihydrate and the sugar, with water.

The invention is illustrated by the following Examples:

EXAMPLE 1

Granulate

| Component | Weight (g) |
| --- | --- |
| Amoxicillin trihydrate | 200 |
| Sucrose | 800 |

Amoxicillin trihydrate and sucrose are sieved together through 1.0 mm sieve, mixed in a tumbler mixer and afterwards extruded through the extruder (Theysohn TSK N20/20D—Maschinenbau/Salzgitter (Germany)) by water flow rate of 1 g/min and a resulting mass flow of 30 g/min.

The obtained wet mass is screened by using an oscillating sieve through a 2.0 mm sieve and dried in a fluid bed dryer with an inlet air temperature of 60° C. about 5 min. After drying, the extruded product obtained is screened once again through a 1 mm oscillating sieve and then homogenized in a tumbler mixer to obtain granulate of amoxicillin trihydrate.

EXAMPLE 2

Granulate

| Component | Weight (g) |
| --- | --- |
| Amoxicillin trihydrate | 100 |
| Sucrose | 900 |

Solution for extrusion granulation:

| Component | Weight (g) |
| --- | --- |
| Water | 100 |
| Sucrose | 200 |

200 g sucrose is dissolved in 100 g warm water and allowed to cool to room temperature to obtain solution for extrusion (stock solution, only a part is needed for extrusion—approximately 35 g).

Amoxicillin trihydrate and sucrose are sieved together through 1.0 mm sieve, mixed in a tumbler mixer and afterwards extruded through the extruder (Theysohn TSK N20/20D) by preliminary prepared aqueous sucrose solution and flow rate of 3 g/min and a resulting mass flow of 30 g/min.

The obtained wet mass is screened by using an oscillating sieve through 2.0 mm sieve and dried in a fluid bed dryer with an inlet temperature of 60° C. about 5 min. After drying, extruded product is screened once again through 1.0 mm oscillating sieve and then homogenized in a tumbler mixer to obtain granulate.

EXAMPLE 3

Granulate

| Component | Weight (kg) |
|---|---|
| Amoxicillin trihydrate | 20 |
| Sucrose | 80 |

Solution for extrusion granulation:

| Component | Weight (kg) |
|---|---|
| Water | 10 |
| Sucrose | 20 |

20 kg sucrose is dissolved in 10 kg warm water and allowed to cool to room temperature to obtain solution for extrusion (stock solution, only a part is needed for extrusion—approximately 12 kg).

Amoxicillin trihydrate and sucrose are sieved together through 1.0 mm sieve, mixed in a tumbler mixer and afterwards extruded through the extruder (Werner Pfeiderer extruder) by preliminary prepared aqueous sucrose solution and flow rate of 12 kg/h and resulting mass flow of 100 kg/h.

The obtained wet mass is screened by using an oscillating sieve through 2 mm sieve and dried in a fluid bed dryer. After drying, the extruded product obtained is screened once again through 1.0 mm oscillating sieve and then homogenized in a tumbler mixer to obtain granulate.

The invention claimed is:

1. A process for preparing a stable granulate for reconstitution with water into an oral aqueous suspension comprising micronized amoxicillin trihydrate and sugar, the process comprising:
    screening a mixture of amoxicillin trihydrate and sugar through a first sieve to provide a sieved mixture;
    extruding the sieved mixture with a granulation liquid comprising water to obtain a wet extruded mass;
    screening the wet extruded mass through a second sieve to provide a sieved wet extruded mass;
    drying the sieved wet extruded mass to form a dried sieved extruded mass; and
    homogenizing the dried sieved extruded mass to obtain a granulate comprising micronized particles of amoxicillin, wherein the granulate is dissolvable in water to form a smooth suspension and wherein the granulate is free of pharmaceutically acceptable excipients other than sugar.

2. The process according to claim 1, wherein the granulation liquid further comprises sugar.

3. The process according to claim 1, wherein the sugar is selected from the group consisting of sucrose, lactose, sugar alcohols and maltodextrins alone or in combination.

4. The process according to claim 1, wherein the sugar comprises sucrose.

5. The process according to claim 1, wherein the sugar comprises mannitol or sorbitol.

6. The process according to claim 1, wherein the micronized amoxicillin trihydrate is present in an amount of from 1 to 80% by weight of the granulate.

7. The process according to claim 1, wherein the micronized amoxicillin trihydrate is present in an amount of from 5 to 50% by weight of the granulate.

8. The process according to claim 1, wherein the micronized amoxicillin trihydrate is present in an amount of from 10 to 30% by weight of the granulate.

9. The process according to claim 1, wherein the sugar comprises sucrose, and the sucrose is present in an amount of from 20 to 99% by weight of the granulate.

10. The process according to claim 1, wherein the particle size of the granulate is in the range of from 200 to 3000 μm.

11. The process according to claim 1, wherein the particle size of the granulate is in the range of from 500 to 1500 μm.

12. The process according to claim 1, wherein the water in the granulation liquid is added in an amount to compensate for the loss of crystallization water of the amoxicillin trihydrate caused by extrusion.

13. The process according to claim 1, wherein the process is conducted without the use of grinding or micronizing the mixture of amoxicillin trihydrate and sugar.

14. The process according to claim 1, wherein the extrusion is conducted at a temperature between 30° C. to 100° C.

15. The process according to claim 1, wherein the homogenization is conducted in a tumbler mixer.

16. The process according to claim 1, wherein the first and second sieves have a mesh size between 0.5 mm to 4.0 mm.

17. The process according to claim 1, wherein the first and second sieves have a mesh size of 1 mm to 2 mm.

18. A process for preparing a stable granulate for reconstitution with water into an oral aqueous suspension comprising micronized amoxicillin trihydrate and sugar, the process comprising:
    screening a mixture of amoxicillin trihydrate and sugar through a first sieve to provide a sieved mixture;
    extruding the sieved mixture with a granulation liquid comprising water to obtain a wet extruded mass;
    screening the wet extruded mass through a second sieve to provide a sieved wet extruded mass;
    drying the sieved wet extruded mass to form a dried sieved extruded mass; and
    homogenizing the dried sieved extruded mass to obtain a granulate comprising micronized particles of amoxicillin, the particles of amoxicillin having a size range of between 0.1 μm to 100 μm, wherein the granulate is dissolvable in water to form a smooth suspension and wherein the granulate is free of pharmaceutically acceptable excipients other than sugar.

19. The process according to claim 18, wherein the particles of amoxicillin having a size range of between 0.5 μm to 50 μm.

20. The process according to claim 18, wherein major particles of amoxicillin having a size within a range of from 1 μm to 30 μm.

* * * * *